United States Patent
Sankaran et al.

(10) Patent No.: US 11,423,805 B2
(45) Date of Patent: Aug. 23, 2022

(54) SYSTEMS AND METHODS FOR MODELING NUTRIENT TRANSPORT AND/OR PREDICTING WEIGHT CHANGE

(71) Applicant: HeartFlow, Inc., Redwood City, CA (US)

(72) Inventors: Sethuraman Sankaran, Palo Alto, CA (US); Christopher Zarins, Menlo Park, CA (US); Charles A. Taylor, Atherton, CA (US); Leo Grady, Millbrae, CA (US)

(73) Assignee: Heartflow, Inc., Redwood City, CA (US)

( * ) Notice: Subject to any disclaimer, the term of this patent is extended or adjusted under 35 U.S.C. 154(b) by 1146 days.

(21) Appl. No.: 15/673,637

(22) Filed: Aug. 10, 2017

(65) Prior Publication Data

US 2018/0047304 A1    Feb. 15, 2018

Related U.S. Application Data

(60) Provisional application No. 62/373,012, filed on Aug. 10, 2016.

(51) Int. Cl.
| | | |
|---|---|---|
| *G09B 23/30* | (2006.01) | |
| *G16H 50/50* | (2018.01) | |
| *G16H 50/20* | (2018.01) | |
| *G09B 9/00* | (2006.01) | |
| *G06N 20/00* | (2019.01) | |
| *G06N 5/04* | (2006.01) | |

(52) U.S. Cl.
CPC ............ *G09B 23/303* (2013.01); *G09B 9/00* (2013.01); *G16H 50/20* (2018.01); *G16H 50/50* (2018.01); *G06N 5/048* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 8,315,812 B2 | 2/2012 | Taylor | |
| 9,424,395 B2 | 8/2016 | Sankaran | |
| 2015/0038860 A1 | 2/2015 | Fonte | |
| 2016/0224753 A1* | 8/2016 | Grady | A61B 5/021 |
| 2017/0249445 A1* | 8/2017 | Devries | G16H 20/60 |

OTHER PUBLICATIONS

Mabotuwana et al. (BioMedical Engineering OnLine (2007) vol. 6:17; 12 pages).*
Rietjens et al. (Mol Nutr. Food Res. (2011) vol. 55:941-956).*
The effect of weight loss on renal function in patients with severe obesity, Chagnag et. al., Am. Soc. Nephrol., Jun. 2003;14(6):1480-6.
Abdominal Angina—Diagnosis and Surgical treatment, Morris and DeBakey, JAMA, 1961; vol. 176:89-94.
D. Winne, The permeability coefficient of the wall of a villous membrane, Journal of Mathematical Biology, vol. 6, pp. 95-108, 1978.
Ni et.al., Theoretical model studies of intestinal drug absorption V. Non-steady-state fluid flow and absorption, International J. of Pharmacology, vol. 5, pp. 33-47, 1980.
D.G. Levitt, Quantification of small intestinal permeability during normal human drug absorption, BMC Pharmacology and Toxicology, 14:34, 2016.
Minekus, Mans; "A multicomparmental dynamic computer-controlled model simulating the stomach and small intestine", Alternatives to laboratory animals: ATLA, Jan. 1, 1995 (Jan. 1, 1995), pp. 197-209, retrieved from URL:https://www.researchgate.net/profile/Robert_Havenaar/publication/256911534_A_multicompartmental_Dynamic_computer-controlled_mode_simulating_the_stomach_and_small_intestine_ATLA_Altern_Lab_Anim (retrieved on Nov. 6, 2017).
Aurelie, Guerra et al., "Relevance and challenges in modeling human gastric and small intestinal digestion", Trends in Biotechnology, vol. 30, No. 11, Nov. 1, 2012 (Nov. 1, 2012), pp. 591-600.

* cited by examiner

*Primary Examiner* — Lori A. Clow
(74) *Attorney, Agent, or Firm* — Bookoff McAndrews, PLLC

(57) ABSTRACT

Systems and methods are disclosed for identifying and modeling unresolved vessels, and the effects thereof, in image-based patient-specific hemodynamic models. One method includes: receiving a patient-specific anatomical model of at least a portion of a visceral vascular system of the patient; receiving patient-specific information related to the patient's food intake; generating a patient-specific model of blood flow in the patient-specific anatomical model of the portion of the visceral vascular system of the patient; generating a patient-specific model of nutrient transport from at least a part of a gastrointestinal system of the patient to the portion of the visceral vascular system of the patient based on the patient-specific information related to the patient's food intake; and determining an indicia of energy available in the patient based on the patient-specific model of nutrient transport.

20 Claims, 7 Drawing Sheets

SYSTEMS AND METHODS FOR MODELING NUTRIENT TRANSPORT AND/OR PREDICTING WEIGHT CHANGE

RELATED APPLICATION(S)

This application claims priority to U.S. Provisional Application No. 62/373,012 filed Aug. 10, 2016, the entire disclosure of which is hereby incorporated herein by reference in its entirety.

FIELD OF THE DISCLOSURE

Various embodiments of the present disclosure relate generally to modeling of physiological systems. More specifically, particular embodiments of the present disclosure relate to systems and methods for modeling nutrient transport and/or predicting weight change.

BACKGROUND

The visceral system plays an important role in the transfer of nutrients from food to the blood stream, and therefore in weight loss and/or weight gain in individuals. Various factors may contribute to the mechanism by which weight loss and/or weight gain occurs, at least within the visceral vascular system. These factors may include: (i) the efficiency of digestive enzymes, (ii) the diffusion of the nutrients into the blood stream; (iii) the flow rate through the small intestine, mesenteric artery, celiac artery, iliac artery, the portal veins, and/or the hepatic veins; (iv) the characteristics of the arteries and/or veins; (v) the characteristics of blood transport and cellular metabolism, including efficiency; (vi) evidence and/or characteristics of peristalsis; (vii) the basal metabolic rate; and/or (viii) any preexisting conditions, e.g., insulin resistance. More specifically, energy and metabolic efficiency may be understood by the mechanism of energy transfer in the visceral vascular system, and the processing of nutrients in the liver.

One of the causes for weight loss may be related to mesenteric ischemia. Mesenteric ischemia may present itself as postprandial pain due to the inability for blood flow in mesenteric artery to increase in response to the need for increased blood flow during the digestive process, thus impairing the ability to absorb nutrients from the small intestine. In other words, the arterial blood flow may not be able to meet visceral blood demand. Weight loss may also be caused by obstruction in the portal venous system or hepatic artery, impairing the delivery of nutrients to the liver which processes the absorbed nutrients. The inability to process nutrients in the liver, e.g., during insulin resistance, may also contribute to weight loss or gain.

SUMMARY

Described below are various embodiments of the present disclosure of a system and method that aids in modeling blood flow and its relationship to weight gain or loss. According to certain aspects of the present disclosure, systems and methods are disclosed for modeling nutrient transport within a patient.

One method includes: receiving, in an electronic storage medium, a patient-specific anatomical model of at least a portion of a visceral vascular system of the patient; receiving, in an electronic storage medium, patient-specific information related to the patient's food intake; generating a patient-specific model of blood flow in the patient-specific anatomical model of the portion of the visceral vascular system of the patient; generating a patient-specific model of nutrient transport from at least a part of a gastrointestinal system of the patient to the portion of the visceral vascular system of the patient based on the patient-specific information related to the patient's food intake; and determining an indicia of energy available in the patient based on the patient-specific model of nutrient transport.

In accordance with another embodiment, a system for modeling nutrient transport within a patient comprises: a data storage device storing instructions for modeling nutrient transport within a patient; and a processor configured for: receiving, in an electronic storage medium, a patient-specific anatomical model of at least a portion of a visceral vascular system of the patient; receiving, in an electronic storage medium, patient-specific information related to the patient's food intake; generating a patient-specific model of blood flow in the patient-specific anatomical model of the portion of the visceral vascular system of the patient; generating a patient-specific model of nutrient transport from at least a part of a gastrointestinal system of the patient to the portion of the visceral vascular system of the patient based on the patient-specific information related to the patient's food intake; and determining an indicia of energy available in the patient based on the patient-specific model of nutrient transport.

In accordance with another embodiment, a non-transitory computer readable medium for use on a computer system containing computer-executable programming instructions for performing a method of modeling nutrient transport within a patient, the method comprising: receiving, in an electronic storage medium, a patient-specific anatomical model of at least a portion of a visceral vascular system of the patient; receiving, in an electronic storage medium, patient-specific information related to the patient's food intake; generating a patient-specific model of blood flow in the patient-specific anatomical model of the portion of the visceral vascular system of the patient; generating a patient-specific model of nutrient transport from at least a part of a gastrointestinal system of the patient to the portion of the visceral vascular system of the patient based on the patient-specific information related to the patient's food intake; and determining an indicia of energy available in the patient based on the patient-specific model of nutrient transport.

According to certain aspects of the present disclosure, systems and methods are disclosed for planning treatment of a lesion.

One method includes: receiving, in an electronic storage medium, a patient-specific anatomical model of at least a portion of a visceral vascular system of a patient; identifying one or more lesions in the patient-specific anatomical model suspected of affecting blood flow to at least a part of the gastrointestinal system of the patient; and performing one or more iterations of: (1) selecting one or more lesions of the identified lesions; (2) determining a healthy diameter of a blood vessel lumen at a location of the one or more lesions of the identified lesions; (3) generating an anatomical model of a treatment of the one or more lesions using the determined healthy diameter; and (4) determining and outputting, into an electronic storage medium, an indicia of the energy available in the patient, based on the treatment of the one or more lesions.

In accordance with another embodiment, a system for planning treatment of a lesion comprises: a data storage device storing instructions for planning treatment of a lesion; and a processor configured for: receiving, in an electronic storage medium, a patient-specific anatomical model of at least a portion of a visceral vascular system of a patient; identifying one or more lesions in the patient-specific anatomical model suspected of affecting blood flow to at least a part of the gastrointestinal system of the patient; and performing one or more iterations of: (1) selecting one or more lesions of the identified lesions; (2) determining a healthy diameter of a blood vessel lumen at a location of the one or more lesions of the identified lesions; (3) generating an anatomical model of a treatment of the one or more lesions using the determined healthy diameter; and (4) determining and outputting, into an electronic storage medium, an indicia of the energy available in the patient, based on the treatment of the one or more lesions.

In accordance with another embodiment, a non-transitory computer readable medium for use on a computer system containing computer-executable programming instructions for planning treatment of a lesion, the method comprising: receiving, in an electronic storage medium, a patient-specific anatomical model of at least a portion of a visceral vascular system of a patient; identifying one or more lesions in the patient-specific anatomical model suspected of affecting blood flow to at least a part of the gastrointestinal system of the patient; and performing one or more iterations of: (1) selecting one or more lesions of the identified lesions; (2) determining a healthy diameter of a blood vessel lumen at a location of the one or more lesions of the identified lesions; (3) generating an anatomical model of a treatment of the one or more lesions using the determined healthy diameter; and (4) determining and outputting, into an electronic storage medium, an indicia of the energy available in the patient, based on the treatment of the one or more lesions.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIG. 6 may depict an exemplary method of performing step 308 of method 300 in FIG. 3.

Figure 1:
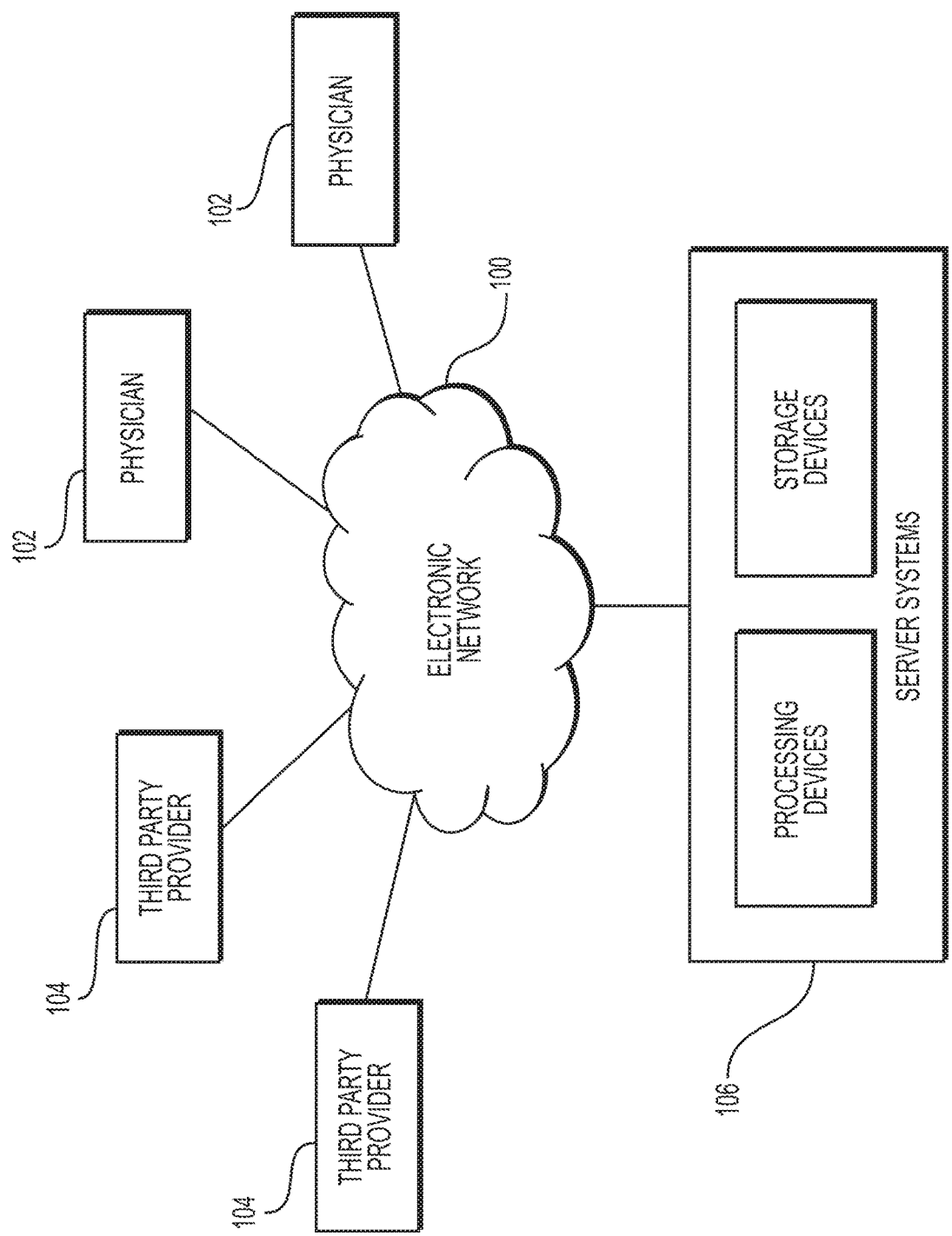
FIG. 1 is a block diagram of an exemplary system and network for predicting weight gain and/or weight loss through modeling the visceral system, according to an exemplary embodiment of the present disclosure.

The steps described in the methods may be performed in any order, or in conjunction with any other step. It is also contemplated that one or more of the steps may be omitted for performing the methods described in the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Various embodiments of the present disclosure may provide systems and methods for modeling nutrient transport and/or predicting weight change, e.g., through modeling the visceral system. Some embodiments of the present disclosure may include a patient-specific prediction of energy transfer and metabolism by modeling the visceral and the portal system. At least some of the systems and methods of the present disclosure may include a predictive modeling approach that accounts for flow-rates through various vessels (e.g., in the visceral vascular system and the hepatic arteries and veins), diffusion and/or transport through the villi and micro-villi, and peristalsis to quantify the fraction of intake energy that is converted into useful energy. Some embodiments may include a system and method of predicting the propensity for weight gain or loss by modeling the mismatch between the net energy transferred and energy demand and metabolism. Some embodiments may include a system and method that may take as an input data from any imaging modality, including, but not limited to, CT scan, ultrasound, angiogram, MRI etc., from which the geometry of all the vessels of interest in the visceral system may be extracted. Subsequently, the blood demand in each of the vessels (e.g., mesenteric, celiac, iliac etc.) may be modeled. Blood demand may be based on scaling laws based on patient and organ size, direct measurement of flow using techniques such as Doppler ultrasound, or by scaling cardiac output with population-averaged flow-splits. The blood demand in the visceral system may also be driven by hormonal signals related to food ingestion and stage of digestive cycle, such as postprandial hyperemia. Artery size may change during fasting, and/or when CT scan is performed, but may increase in size after meals, as the blood flow increases. The effect of postprandial hyperemia may also be taken into account when modeling organ demand. The spatial distribution of flow-rates may be obtained by using computational fluid dynamics methods (e.g., using boundary conditions directly derived as described above). In some embodiments, the spatial distribution of flow-rates may be obtained by using reduced order models of blood flow, machine learning methods, etc. The absorption of nutrients into the blood stream may occur through villi and microvilli, distributed through the small intestine. The breakdown of food into nutrients may occur in the small intestine. The nutrients may further diffuse or be transported into the main blood stream. A fast rate of flow (e.g. liquids) in the small intestine may hinder the proper absorption of nutrients into the blood stream. Blockage in any of the arteries may result in insufficient nutrient absorption, which may result in a poor metabolic state. Further, the nutrients may be transported to the liver using the portal veins, which may then be delivered to the systemic circulation via the hepatic veins. By modeling blood flow patterns downstream, we may also be able to assess and identify specific regions based on the nutrient supply and demand.

Referring now to the figures, FIG. 1 depicts a block diagram of an exemplary system 100 and network for predicting weight gain and/or weight loss through modeling the visceral system, according to an exemplary embodiment. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific and/or reference anatomical images and/or information, including, but not limited to, geometrical and/or anatomical characteristics of the vessels of interest of a patient (e.g., mesenteric artery, celiac artery, iliac artery, portal vein, hepatic artery, hepatic vein, etc.).

Physicians 102 and/or third party providers 104 may transmit the anatomical images and/or information on vessels of interest to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
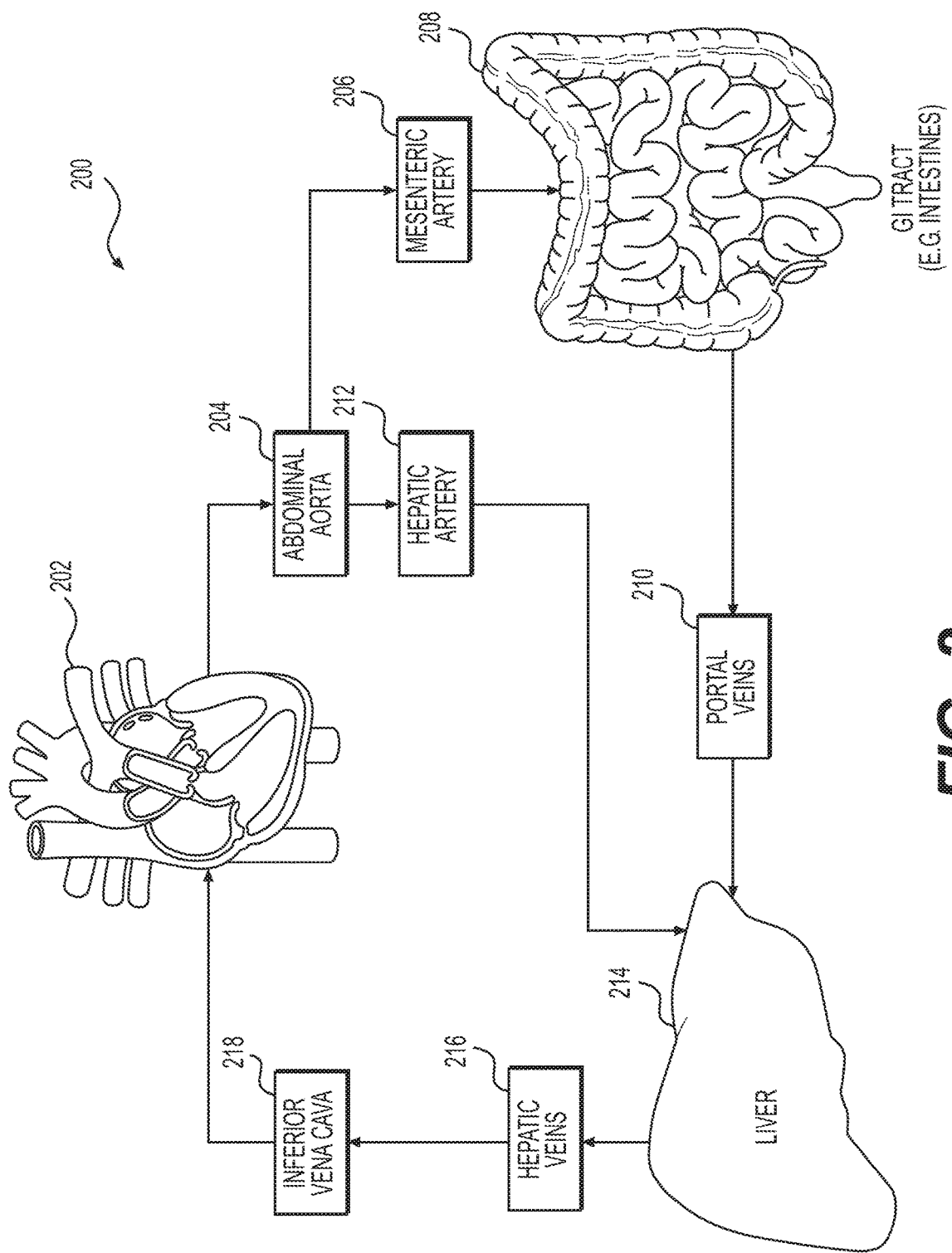
FIG. 2 is an illustration of at least some of the vessels and other anatomical parts of the visceral system that are pertinent to predicting weight gain or weight loss, according to an exemplary embodiment of the present disclosure.

FIG. 2 is an illustration of at least some of the vessels and other anatomical parts of the cardiovascular and visceral system that are pertinent to predicting weight gain or weight loss, according to an exemplary embodiment of the present disclosure. The visceral system may include, various parts of the GI tract (e.g., intestines 208 (small and large), esophagus, stomach, pancreas, etc.), and the liver 214. The visceral vascular system depicted in FIG. 2 may include the heart, and various blood vessels servicing and/or transporting nutrients from or to the organs of the visceral system. For example, the abdominal aorta 204 may carry blood towards the hepatic artery 212 and mesenteric artery 206. The hepatic artery 212 may carry blood to the liver 214 and the mesenteric artery 206 may carry blood to parts of the GI tract (e.g., intestines 208). The mesenteric artery 206 and/or emanating vessels from the mesenteric artery 206 (e.g., capillaries, venules, portal veins 210, etc.) may receive nutrients from parts of the GI tract (e.g., intestines 208). Once the nutrients are received, the resulting vessels (e.g., portal veins 210) may deliver blood and nutrients to the liver 214, where some nutrients may be processed and where blood (e.g., its contents) may be metabolized. Thereafter, the resulting nutrients may be carried by the hepatic veins 216 towards the inferior vena cava 218 and to the heart 202 and then on to the systemic circulation. In various embodiments, the systemic circulation may refer to the overall circulatory system that carries oxygenated blood throughout the body and returns deoxygenated blood the heart. Moreover, the net energy available in the systemic circulation after nutrient transport may be used to predict a change in a weight or mass of a patient following a food intake.

Thus, in some embodiments, the liver may receive oxygenated blood from the hepatic artery and nutrient filled, non-oxygenated blood via the portal vein, as the blood in the portal veins may have been deoxygenated going through the capillary bed in the intestines.

Other parts of the visceral system not shown in FIG. 2 may be useful and considered in embodiments of the present disclosure. These parts include, for example, the pancreas and the stomach. For example, blood may flow towards the pancreas via the pancreaticoduodenal vessels, which may arise from the celiac artery. Inadequate nutrient blood flow to the pancreas could impair the production of digestive enzymes, normally produced by the pancreas. These digestive enzymes may assist in the digestive process in various parts of the GI tract (e.g., in the duodenum and small intestine). For example, while the stomach may aid in digestion by breaking down ingested food in the stomach's acidic environment, the ingested nutrients may be further digested and/or processed for absorption using the digestive enzymes at the microvilli, which is downstream of the stomach in the GI tract. As the food is digested and/or processed at the microvilli, nutrients may enter the portal venous system.

Figure 3:
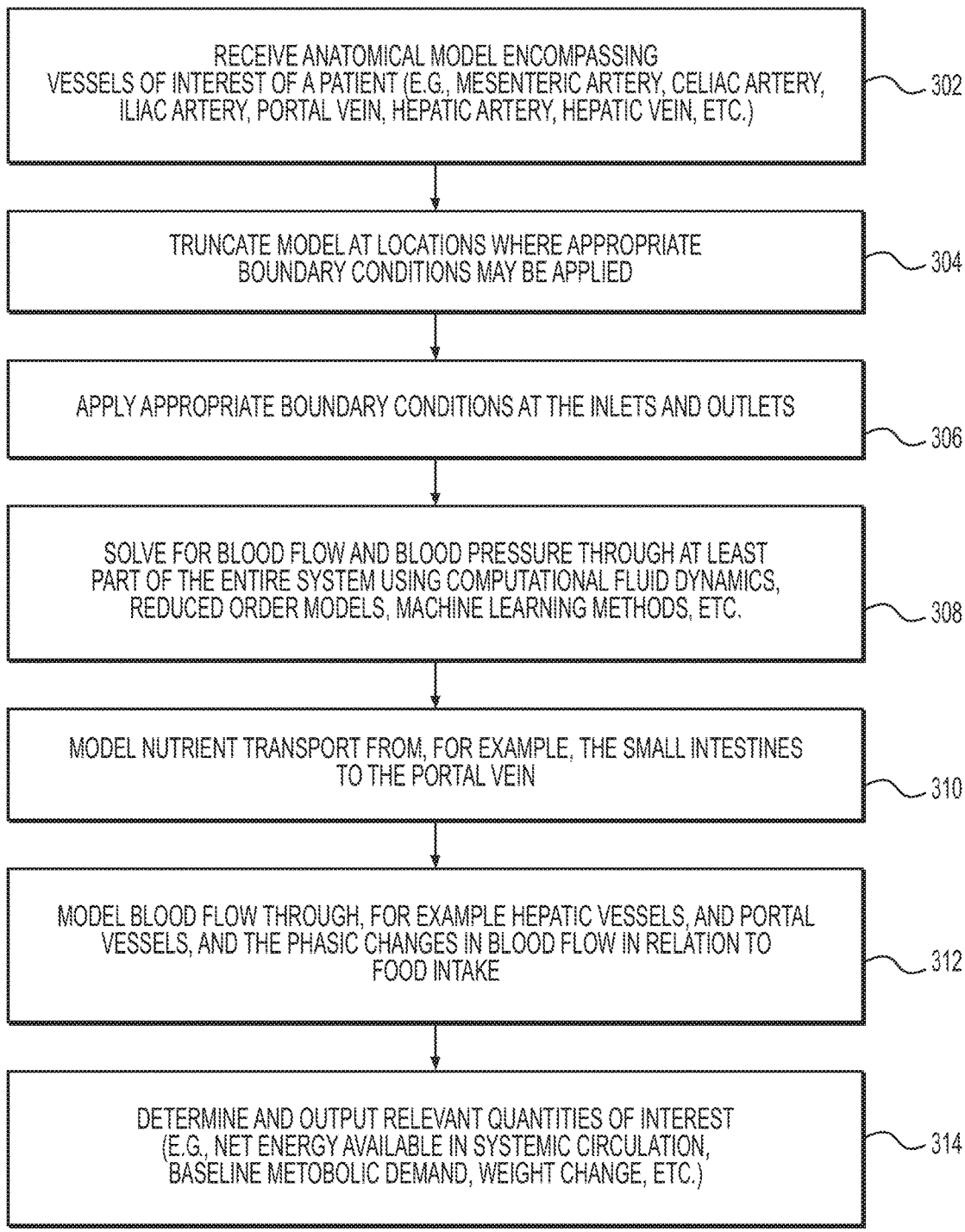
FIG. 3 is a block diagram of a general method of predicting weight gain and/or weight loss through modeling the visceral system, according to an exemplary embodiment of the present disclosure.

Still referring to FIG. 2, at least some embodiments of the present disclosure may be explained as various methods further below, and these methods may reference various features of FIG. 2. For example, method 300 of FIG. 3 provides a general embodiment for predicting weight gain and/or weight loss through modeling the visceral system, and includes solving for blood flow and pressure through a vessel of interest of a patient (e.g., in step 308), including, for example, the hepatic artery 212, mesenteric artery 206, portal veins 210, and hepatic veins 216. Method 400 of FIG. 4 further describes the process of modeling nutrient intake into vessels emanating from the mesenteric artery 206 (e.g., portal veins 210) at parts of the GI tract (e.g., intestines 208). Method 500 describes the process of modeling blood flow through the hepatic vessels and portal vessels (e.g., hepatic arteries 212, hepatic veins 216, portal veins 210, etc.) and any phasic changes in blood flow in relation to food intake. In some embodiments, method 500 may incorporate information regarding the functioning of the liver 214.

FIG. 3 is a block diagram of a general method of predicting weight gain and/or weight loss through modeling the visceral system, according to an exemplary embodiment of the present disclosure. The method of FIG. 3 may be performed by server systems 106, based on information, images, and data received from physicians 102 and/or third party providers 104 over electronic network 100.

Step 302 may include receiving an anatomical model that includes at least the vessels of interest of a patient. In one embodiment, the anatomical model may be generated from received or stored anatomic images and/or information encompassing the vessels of interest of a patient. In such embodiments, the anatomic images and/or information may be stored in an electronic storage medium. The vessels of interest may include, for example, the mesenteric artery, celiac artery, iliac artery, portal vein, hepatic artery, hepatic vein, and/or any vessel involved in the digestive process. The anatomical images and/or information may be extracted from images and/or image data generated from a scanning modality (e.g., forms of magnetic resonance (MR), forms of computed tomography (CT), forms of positron emission tomography (PET), X-Ray, etc.) and/or may be received from an electronic storage device (e.g. hard drive). Step 302 may further include using the anatomical images and/or information to generate a model that includes, at least, the vessels of interest. The process of generating a model may include various segmentation techniques to capture areas of interest from an image or image data.

Step 304 may include truncating the model at locations where appropriate boundary conditions may be applied. In some embodiments, the truncation may be performed such that the regions encompassing the vessels of interest can be captured. For example, intensity variation may be used to detect vessels of interest (e.g., the mesenteric artery, celiac artery, iliac artery, portal vein, hepatic artery, hepatic vein, etc.). In some embodiments, the truncation may be performed such that regions of vessel narrowing may be captured. For example, the truncation may be performed such that the regions distal to the locations of disease in the arteries, and/or regions encompassing the blood vessels of interest can be captured.

Step 306 may include applying appropriate boundary conditions at the boundaries. The boundary conditions provide information about the hemodynamics at the boundaries of the three dimensional model, e.g., the inflow boundaries or inlets, the outflow boundaries or outlets, the vessel wall boundaries, etc. The inflow boundaries or inlets may include the boundaries through which flow is directed into the anatomy of the three-dimensional model, such as at the aorta. The inflow boundary may be assigned, e.g., with a prescribed value or field for velocity, flow rate, pressure, or other characteristic, for example, by coupling a heart model and/or a lumped parameter model to the boundary, etc. The flow rate at the aorta may be estimated by cardiac output, measured directly or derived from the patient's mass using scaling laws. In some embodiments, flow rate of the aorta may be estimated by cardiac output using methods described in U.S. Pat. No. 9,424,395, incorporated by reference in entirety herein. This is described in sensitivity/guided sensitivity patent.

For example, net cardiac output (Q) can be calculated from body surface area (BSA) as $$Q = \frac{1}{60} BSA^{1.15} \text{(cardiac output)}.$$

The body surface area (BSA) may be calculated from height (h) and weight (w) as:

$$BSA = \sqrt{\frac{hw}{3600}}.$$

Coronary flow rate ($q_{cor}$) can be calculated from myocardial mass ($m_{myo}$) as:

$$q_{cor} = c_{dil} \frac{5.09}{60} m_{myo}^{0.75},$$

where $c_{dil}$ is a dilation factor. Thus, the flow in the aorta can be $Q-q_{cor}$.

While the flow rate of the aorta may be estimated from the cardiac output, the distribution of flow in the various branches of the aorta may vary greatly depending on the physiologic state (rest vs exercise vs postprandial) of the patient. After eating, the demand of the visceral system for more blood flow via the celiac, superior mesenteric artery (SMA) and inferior mesenteric artery (IMA) vessels for food digestion may increase. If this increase in blood flow in the post-prandial state cannot be achieved (ie, restricted arterial blood flow, then digestion and nutrient absorption may not take place, and this may result in weight loss. The "postprandial hyperemic state" may be similar to the hyperemia which is needed by the heart and skeletal muscles during exercise.

The outflow boundaries (e.g., outlets) may include the boundaries through which flow is directed outward from the anatomy of the model, such as towards vessels of interest. Each outflow boundary can be assigned, e.g., by coupling a lumped parameter or distributed (e.g., a one-dimensional wave propagation) model. The outlet conditions may include the blood pressure, flow rate, or a combination thereof (e.g. resistance, which is the ratio of pressure to flow). The prescribed values for the inflow and/or outflow boundary conditions may be determined by noninvasively measuring physiologic characteristics of the patient, such as, but not limited to, cardiac output (the volume of blood flow from the heart), blood pressure, etc. The vessel wall boundaries may include the physical boundaries of the vessels of interest.

Furthermore, the blood flow rate, velocity, and blood pressure in the mesenteric artery may be quantified, and may be used as a predictor of mesenteric ischemia. The effect of postprandial hyperemia along with organ size and demand may be used to model the boundary conditions. For example, baseline flow may be modeled using fasting mesenteric flow conditions. The boundary conditions would then be changed to reflect the postprandial maximal hyperemic state. Larger organs would have larger vessels supplying them at rest It is contemplated that in various embodiments or circumstances, there may be a relationship between artery size, flow demand and downstream boundary condition. Postprandial hyperemia may result in an increase in the size of the mesenteric arteries, relative to the other arteries which may not be at hyperemic state. Hence, the boundary resistance may be modeled as being inversely proportional to the outlet area. Further, the baseline arterial size may be reflective of the flow demand.

Step 308 may include solving for blood flow and blood pressure through at least parts of the system using one or more of computational fluid dynamics, reduced order models, machine learning methods, etc. For example, step 308 may include using the boundary conditions calculated in step 306 to solve the equations governing blood flow for velocity and pressure. In one embodiment, step 308 may include the computing of a blood flow velocity field or flow rate field for one or more points or areas of the anatomic model, using the assigned boundary conditions. This velocity field or flow rate field may be the same field as computed by solving the equations of blood flow using the physiological and/or boundary conditions provided above. Step 308 may further include solving scalar advection-diffusion equations governing blood flow at one or more locations of the patient-specific anatomic model.

Alternatively or additionally, the vessels of interest may be simplified to a lumped parameter and/or reduced order model, e.g., an electric circuit. The calculated boundary conditions from step 306, pressure differences, and/or stenotic segments may be modeled as various components on the lumped parameter and/or reduced order model, e.g., resistors on an electronic circuit.

Figure 6:
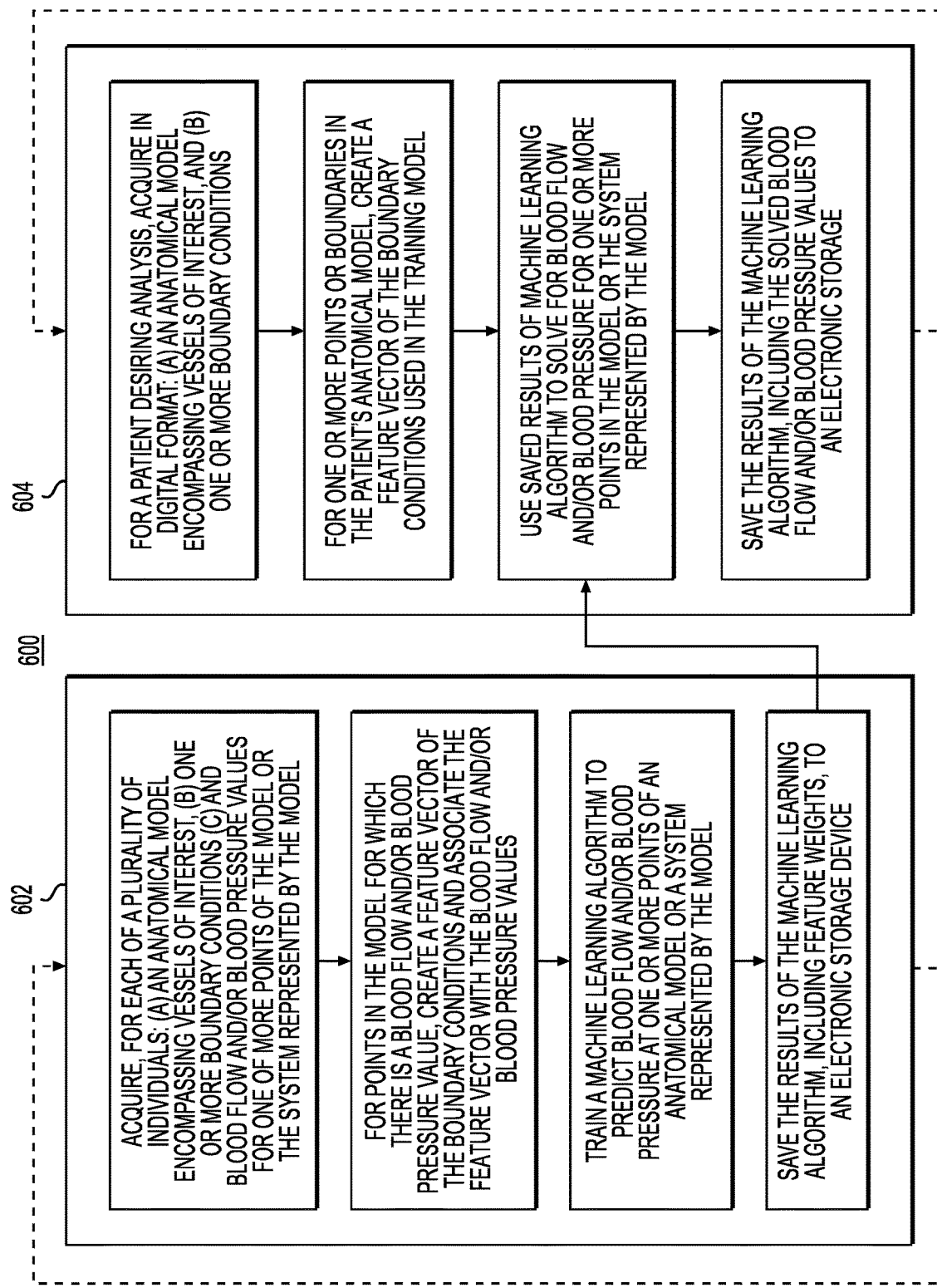
FIG. 6 is a block diagram of an exemplary method of training and applying a machine learning algorithm using boundary conditions to solve for blood flow and blood pressure, according to an exemplary embodiment of the present disclosure.

Alternatively or additionally, the boundary conditions calculated in step 306 may be incorporated into or may be used to form feature vectors to predict blood flow and/or blood pressure at one or more points of a model. In such embodiments, population-based measurements of boundary conditions, blood flow, and blood pressure may be used, for example, in training a machine learning algorithm. Method 600 as depicted in FIG. 6 further describes solving for blood flow and blood pressure using machine learning methods.

Step 310 may include modeling nutrient transport and/or net energy transfer from, for example, the small intestines to blood vessels. The blood vessels may include, for example, the mesenteric artery, iliac artery, celiac artery, and/or vessels emanating from the arteries (e.g., portal veins, capillaries, etc.). It is also contemplated that in some embodiments, nutrient transport and/or net energy transfer from other parts of the GI tract (e.g., stomach, large intestines, etc.) to blood vessels may also be modeled. The concentration of nutrients as they pass through the intestine may be modeled using the following differential equation that combines convection and dispersion of the nutrients within the intestine with the dispersion of nutrients across the villi and microvilli. This differential equation may be written as ([1,2,3])

$$A\frac{dc}{dt} = AD\frac{d^2c}{dt^2} - Q\frac{dc}{dx} - Pc\frac{dA}{dr} \quad (1)$$

where c is the concentration of nutrients in the intestine, A is the cross sectional area, D is the molecular diffusivity, Q is the flow-rate in the intestine, and P is the permeability of the membrane comprising of the villi and microvilli.

The number of particles that have diffused into a blood vessel (e.g., mesenteric artery), n, in a given time window, $\Delta t$, may be modeled as ([1,3])

$$n = P2\pi rc\Delta t \quad (2)$$

The particles that may have transferred into the blood vessel from the intestine may be advected using the blood velocity streamlines using the Navier-Stokes equation, $$\frac{\partial c_m}{\partial t} = -v_m \frac{\partial c_m}{\partial x}, \quad (3)$$

where $v_m$ is the blood velocity, and $c_m$ is the concentration of nutrients in the mesenteric artery that may depend on both the location along the mesenteric artery and the phase in the blood flow cycle. Population averaged values of the permeability (P) and convective flow (Q) may be obtained. The rest of the parameters may be derived from either the image segmentation (e.g. A, r), described in detail herein, or from solving fluid-flow equations (e.g. $v_m$).

However, in some embodiments, the nutrient transport may be modeled based on various factors, including, but not limited to: the blood flow, blood pressure, and other hemodynamic characteristics of the mesenteric artery, iliac artery, celiac artery, and vessels emanating from them (e.g., portal veins, capillaries, etc.); the density, shape, content, and/or nutrients contained in the food as it passes through the GI tract, or the temporal and/or environmental aspects during the intake of food ("food intake information"); and gastro-intestinal health information, including the health and/or functional capability of various parts of the GI tract, the peristaltic function of the intestines, and properties of the blood vessel membrane affecting the transfer of nutrients, e.g., membrane channel permeability. Method 400, depicted in FIG. 4, describes an exemplary embodiment of the process of modeling nutrient transport (e.g., step 310) in further detail.

Step 312 may include modeling blood flow through, for example, a hepatic and/or portal vessels. Step 312 may further include modeling the phasic changes in blood flow in relation to food intake (or the digestive process). Blood flow in the portal vein, e.g., the blood flow obtained from step 308, may be used to compute the transport of nutrients into the liver by solving particle advection through the blood, e.g., $$\frac{\partial c_m}{\partial t} = -v_m \frac{\partial c_m}{\partial x},$$

where $v_m$ is the blood velocity, and $c_m$ is the concentration of nutrients in the mesenteric artery that may depend on the location, x, along the mesenteric artery and/or on the phase in the blood flow cycle. In some embodiments, the blood flow through the hepatic and/or portal vessels may depend on liver function (e.g., an indicia of a liver function), which may be assumed to be normal. If there is evidence of abnormal liver function (e.g., if there is an indication of insulin resistance), the effective energy supply of the nutrients may be calculated. The transport of nutrients to the systemic circulation may then be calculated using blood velocity in the hepatic vein.

Step 314 may include determining and outputting relevant quantities of interest from method 300. For example, step 314 may include determining and outputting one or more of the net energy available in the systemic circulation, the net nutrient availability in the blood stream, the basal metabolic rate, and/or the insulin resistance. In some embodiments, the net energy available in the systemic circulation may be calculated using output from step 312 (e.g., the transport of nutrients to the systemic circulation). Since mesenteric ischemia, peristaltic dysfunction, and celiac disease may often be accompanied by weight loss, one embodiment may include modeling peristalsis (e.g., smooth muscle contraction (SMC)) and how blood flow affects peristalsis, or the flow rate in the presence of ischemia or celiac disease. Weight gain may depend on various factors, including, but not limited to, metabolism and/or insulin resistance. In some embodiments, the net nutrient availability in the blood stream may be calculated using the output from step 312 (e.g., the transport of nutrients to the systemic circulation) and may be converted to calories. The basal metabolic rate may be calculated from age, sex, height, weight, etc. The insulin resistance may be calculated from a fasting glucose test. In some embodiments, the relevant quantities of interest, as presently described may be output to an electronic storage medium or display.

The quantities of interest, including the effective permeability and flowrate, the rate of particle transfer to the mesenteric artery, and the concentration of nutrients along all the vessels, which may have been modeled and/or determined in the preceding steps of method 300, may be output to an electronic storage medium or display. In addition, the net energy available in systemic circulation and baseline metabolic demand, which may have been calculated in step 314, may also be output. Weight loss or gain may be calculated as the difference in net energy available in systemic circulation and the baseline metabolic demand. This difference, which may be calculated in calories, may be converted into pounds, kilograms, and/or other metrics, and may be output. A positive value for the difference may imply a weight gain, and a negative value of the difference may imply a weight loss.

Figure 4:
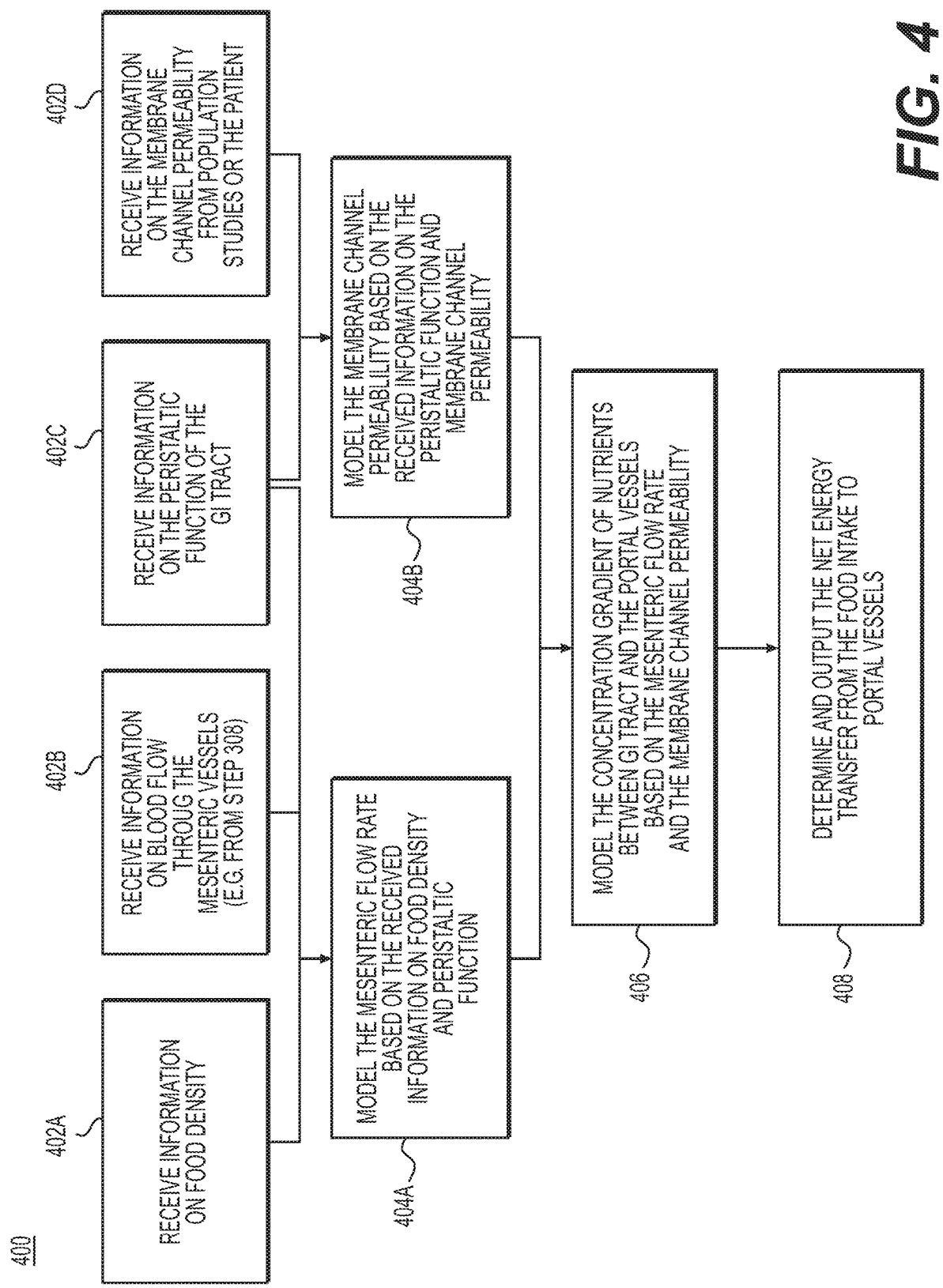
FIG. 4 is a block diagram of a general method 400 of modeling nutrient intake from parts of the gastrointestinal (GI) tract (e.g., the small and large intestines) to the blood vessels (e.g., the portal vein). Method 400 may describe the process of performing step 310 in method 300 in further detail.

FIG. 4 is a block diagram of a general method 400 of modeling nutrient intake from parts of the gastrointestinal (GI) tract (e.g., the small and large intestines) to the blood vessels (e.g., the portal vein). Method 400 may describe the process of performing step 310 in method 300 in further detail. As described in step 310 of method 300, the concentration of nutrients as it passes through the intestine may be modeled using the following differential equation that combines convection and dispersion of the nutrients within the intestine with the dispersion of nutrients across the villi and microvilli, $$A\frac{dc}{dt} = AD\frac{d^2c}{dt^2} - Q\frac{dc}{dx} - Pc\frac{dA}{dr},$$

where c is the concentration of nutrients in the intestine, A is the cross sectional area, D is the molecular diffusivity, Q is the flow-rate in the intestine and P is the permeability of the membrane comprising of the villi and microvilli. However, various factors may influence the amount and the way nutrient is transferred to the blood vessels from the GI tract, including, but not limited to: the blood flow, blood pressure, and other hemodynamic characteristics of the mesenteric artery, iliac artery, celiac artery, and vessels emanating from them; the density, shape, content, and/or nutrients contained in the food as it passes through the GI tract; the health and/or functional capability of various parts of the GI tract, including the peristaltic function of the intestines; and properties of the blood vessel membrane affecting the transfer of nutrients, e.g., membrane channel permeability. While steps 402A-D include receiving information on at least some factors that may influence the transfer of nutrients from the GI tract to the blood vessels, it is contemplated that the factors for which information is received in step 402A-D are not exhaustive.

For example, step 402A may include receiving information on food density. Since liquids tend to pass faster than solids, contact time with the villi and microvilli may be proportional to the density of food and may be modeled as such. This implies that the flowrate, Q in the above recited differential equation, may be modeled as inversely proportional to the food density.

The nutrient transport from the GI tract (e.g., intestines) into the blood vessels may also depend on the blood pressure, blood flow, and other hemodynamic characteristics of the blood vessels leading to the part of the GI tract where the nutrient transfer is taking place. Thus, step 402B may include receiving information on blood flow through the mesenteric vessels (e.g., from step 308 of method 300 as depicted in FIG. 3).

In some embodiments, the nutrient transport may be modeled based on whether peristaltic dysfunction exists. Thus, step 402C may include receiving information on the peristaltic function of the GI tract (e.g., the peristaltic function of the small intestines). For example, if evidence for peristaltic dysfunction may be found, the nutrient intake may be accounted, e.g., by scaling by a peristaltic factor ($\alpha_{perist}$). Other non-linear conversions of the intake factor may also be used. Therefore, in one embodiment, if evidence of peristaltic dysfunction is found, the flowrate Q may be calculated as $Q \equiv \alpha_{perist} f(Q_{norm})$. If evidence of peristaltic dysfunction is not found, the flowrate may be $Q = Q_{norm}$.

Step 404A may include modeling the flow rate, Q, based on the received information, including, for example, the information on blood flow through the mesenteric vessels (e.g., from step 308), food density, and peristaltic function. Other factors, not described in steps 402A-C, may also influence the flow rate, Q. For example, the content of food may directly or inversely affect the flow rate, depending on, for example, lipid content.

In some embodiments, the nutrient transport and/or net energy transfer from the food intake to the portal vein may depend on the concentration gradient and/or on the channel permeability. Thus, step 402D may include receiving information on membrane channel permeability from population studies and/or the patient. The channel permeability may also depend on the health of the villi and/or microvilli, for example, on peristaltic function, as determined in step 402C. Thus, step 404B may include modeling the membrane channel permeability based on the received information on the peristaltic function and membrane channel permeability. In some embodiments, the villi and micro-villi may be assumed to function normally. If there is evidence of disease, such as celiac disease, then there may be a reduced efficiency of energy transfer from the small intestine to the mesenteric artery. In such embodiments, a corrective factor for permeability through the membrane may be used to model this reduced efficiency. A simple linear model or a non-linear model may be used. In such embodiments, the permeability may be modeled as $P \equiv \alpha_{perm} f(P_{norm})$. In some embodiments, if evidence of peristaltic dysfunction is not found, the permeability may be modeled as $P = P_{norm}$.

The concentration gradient may depend on the blood flow, blood pressure, and/or hemodynamic characteristics of the blood vessels, as may be received in step 402B (or from step 308) and/or on the flowrate, Q, as modeled in step 404A. Thus, step 406 may include modeling the concentration gradient of nutrients between the GI tract and the portal vessels based on the flow rate, Q, and the membrane channel permeability.

Step 408 may include determining and outputting the net energy transfer from the food intake to the portal vessels. The net energy transfer may depend on the transfer of nutrients from the small intestines to the blood vessels (e.g., mesenteric vessels, iliac vessels, celiac vessels, portal vessels, capillaries, etc.), and may be converted to calories. Furthermore, the net energy transfer may depend on the type, amount, form, and/or density of nutrients being transferred. The net particles transferred in a given time window, $\Delta t$, may be modeled by solving $n = P 2\pi r c \Delta t$, where c is the concentration of nutrients in the intestine, P is the membrane permeability that may be derived from population averaged values of membrane permeability or from one or more patients, and the radius, r, may be derived from either the anatomical information and/or images received in step 302, for example. In some embodiments, the concentration of nutrients in the blood may be assumed to be zero.

While method 400 demonstrates at least some embodiments of the process of determining the transfer of nutrients and/or net energy transfer from the food intake in the small intestines to some blood vessels (e.g., mesenteric vessels, celiac vessels, iliac vessels, portal vessels, vessels in the villi and microvilli, etc.), it is contemplated that the transfer may occur between any part of the GI tract (stomach, large intestines, etc.) to any blood vessel involved with the transfer of nutrients. In such contemplated embodiments, similar steps as laid out in method 400 may be applied.

Figure 5:
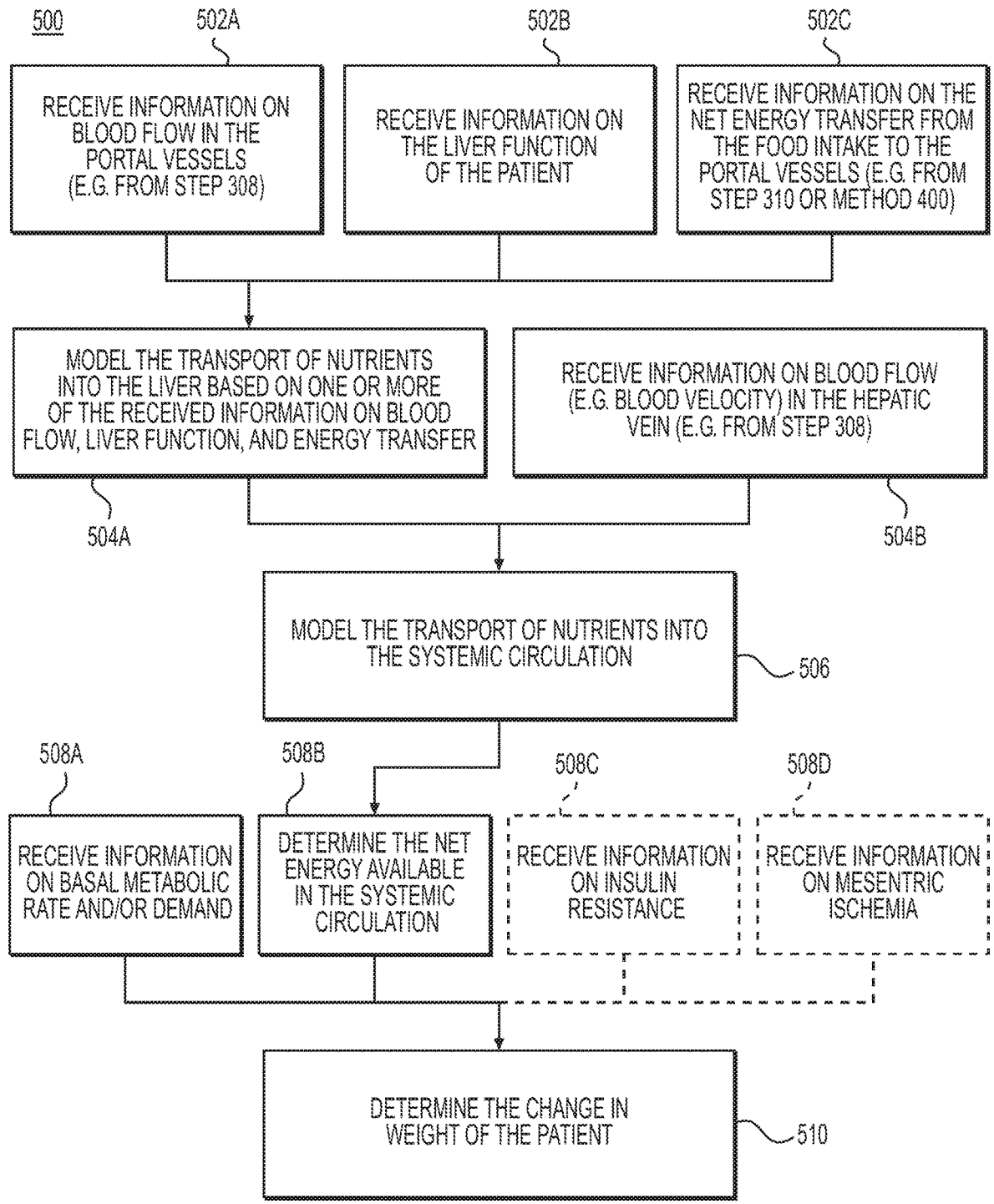
FIG. 5 is a block diagram of a general method 500 of modeling blood flow through the hepatic and portal vessels, and the phasic changes in blood flow in relation to food intake. Method 500 may describe the process of performing step 312 in method 300 in further detail.

FIG. 5 is a block diagram of a general method 500 of modeling blood flow through the hepatic and portal vessels, and the phasic changes in blood flow in relation to food intake. Method 500 may describe the process of performing steps 312 and 314 in method 300 in further detail.

Step 502A may include receiving information on blood flow, blood pressure, and/or other hemodynamic characteristics in the blood vessels delivering blood to and/or originating from the liver (e.g., as in step 308 of method 300 as described in FIG. 3). The blood vessels may include, for example, the hepatic vessels delivering blood from the abdominal aorta to the liver, the hepatic veins carrying filtered blood and nutrients from the liver on to the systemic circulation, and/or the portal vessels delivering blood and nutrients from parts of the GI tract (e.g., small intestine) to the liver. Step 502A may include, for example, calculating the blood velocity in the hepatic arteries and/or hepatic veins.

In some embodiments, the transport of nutrients into the liver may depend on the health and/or functional capability of the liver. Thus, step 502B may include receiving information on the liver function of the patient. The liver function may include, for example, existence and severity of diabetes, or insulin resistance. If there is evidence of abnormal liver function (e.g., if there is an indication of insulin resistance), the effective energy supply of the nutrients may be calculated.

In some embodiments, the transport of nutrients into the liver may be based on the transfer of nutrients and/or net energy transfer from parts of the GI tract (e.g., the small intestine) to blood vessels (e.g., vessels in the villi, microvilli, portal veins, etc.). Thus, step 502C may include receiving information on the net energy transfer (or an indicia of energy transfer) from the food intake to the blood vessels leading to the liver (e.g., portal vein). The information may be received, for example, from method 400 described in FIG. 4 or from step 310 of method 300, as described in FIG. 3.

Step 504A may include modeling the transport of nutrients into the liver based on one or more of the received information on blood flow, liver function, and energy transfer. The transport of nutrients into the liver may be modeled by solving particle advection through the blood, e.g., $$\frac{\partial c_m}{\partial t} = -v_m \frac{\partial c_m}{\partial x},$$

where $v_m$ is the blood velocity, and $c_m$ is the concentration of nutrients in a blood vessel (e.g., mesenteric artery, portal vein, etc.) leading to the liver that may depend on the location, x, along the blood vessel and/or on the phase in the blood flow cycle. The health and/or functional capability of the liver may influence the transport of nutrients, for example, by affecting the effective energy supply of the nutrients.

Step 506 may include modeling the transport of nutrients into the systemic circulation. The transport of nutrients into the systemic circulation may depend, in part, on the blood flow, blood pressure, and/or hemodynamic characteristics (e.g., blood velocity) of blood vessels emanating from the liver (e.g., hepatic vein). Thus step 506 may be based, in part, on step 502A. Alternatively or additionally, in some embodiments, modeling of the transport of nutrients may depend on receiving information on blood flow (e.g., blood velocity) in the hepatic vein (e.g., as in step 504B or step 308 from FIG. 3).

Step 508A may include receiving information on the basal metabolic rate and/or demand. The information may be received from the patient or from population studies. Alternatively or additionally, the basal metabolic rate and/or demand may be determined based on received information including, but not limited to the age, mass, weight, gender, height, genetic information, body fat percentage, etc. of the patient. Step 508B may include determining the net energy available (or an indicia of energy available) in the systemic circulation. The net energy available in the systemic circulation may be based on the transport of nutrients into the systemic circulation, modeled in step 506. The net energy available or indicia of energy available in the systemic circulation or a vasculature (e.g., visceral vascular system) may include, for example, a net nutrient available in the systemic circulation or a vasculature, a net sugar level in the systemic circulation or a vasculature, energy transferred in the visceral vascular system, and/or an indicia of a certain nutrient or metabolic process in a systemic circulation or a vasculature (e.g.,chylomicrons). For example, chylomicrons found in the portal vessels may indicate fat-filled particles, which may cause the portal blood to appear milky white after a meal.

Step 510 may include determining the change in weight of the patient. Weight loss or gain may be calculated as the difference in net energy available in systemic circulation and the baseline metabolic demand. This difference, which may be calculated in calories, may be converted into pounds, kilograms, and/or other metrics, and may be output. A positive value for the difference may imply a weight gain, and a negative value of the difference may imply a weight loss.

In some embodiments, in addition the basal metabolic rate and/or demand and the net energy available in the systemic circulation, the change in weight may depend on other factors, for example, insulin resistance of the patient (e.g., for diabetic patients), and/or information on mesenteric ischemia (e.g., for patients suffering from mesenteric ischemia). In such embodiments, step 508C may include receiving information on insulin resistance. Additionally or alternatively, step 508D may include receiving information on mesenteric ischemia.

FIG. 6 is a block diagram of an exemplary method of training and applying a machine learning algorithm using boundary conditions to solve for blood flow and blood pressure, according to an exemplary embodiment of the present disclosure. FIG. 6 may depict an exemplary method of performing step 308 of method 300 in FIG. 3.

The boundary conditions provide information about the anatomical model at its boundaries, e.g., the inflow boundaries or inlets, the outflow boundaries or outlets, the vessel wall boundaries, etc. Information at each boundary may include, e.g., a prescribed value or field for velocity, flow rate, pressure, or other characteristic, for example, by coupling a heart model and/or a lumped parameter model to the boundary, etc. Method 600 of FIG. 6 may be performed by server systems 106, based on information received from physicians 102 and/or third party providers 104 over electronic network 100.

In one embodiment, the method 600 of FIG. 6 may include a training method 602, for training one or more machine learning algorithms based on boundary conditions measured, estimated, simulated, and/or obtained from numerous patients, and the measured, estimated, simulated, and/or obtained blood flow and/or blood pressure at one or more points of the model, and a production method 604 for using the machine learning algorithm results to solve for the blood flow and/or blood pressure at one or more points of the model, and/or the entire system represented by the model (e.g., as in step 308 of method 300, as described in FIG. 3).

In one embodiment, training method 602 may involve acquiring, for each of a plurality of individuals, e.g., in digital format: (a) an anatomical model encompassing vessels of interest (e.g., mesenteric artery, celiac artery, iliac artery, portal vein, hepatic artery, hepatic vein, etc.), (b) one or more measured, estimated, simulated, and/or obtained boundary conditions (e.g., at the outflow boundaries, inflow boundaries, vessel wall boundaries, etc.) and (c) the measured, estimated, simulated, and/or or obtained blood flow and/or blood pressure at one or more points of the model and/or entire system represented by the model. Training method 602 may then involve, for one or more points or boundaries in each patient's model, creating a feature vector of the patients' boundary conditions at one or more points or boundaries of the anatomical model and associating the feature vector with the blood flow and/or blood pressure values at one or more points of the model or the system represented by the model. Training method 602 may then save the results of the machine learning algorithm, including feature weights, in a storage device of server systems 106. The stored feature weights may define the extent to which boundary conditions and/or anatomical characteristics are predictive of the blood flow and/or blood pressure at one or more points of the model or the system represented by the model.

In one embodiment, the production method 604 may involve estimating blood flow and/or blood pressure values for a particular patient, based on results of executing training method 602. In one embodiment, production method 604 may include acquiring, e.g. in digital format: (a) a patient-specific anatomical model encompassing vessels of interest of the patient (e.g., mesenteric vessels, celiac vessels, iliac vessels, portal vessels, hepatic vessels, etc.), and (b) one or more measured, estimated, simulated, and/or obtained boundary conditions (e.g., at the inflow boundaries, outflow boundaries, vessel wall boundaries, etc.). For multiple points or boundaries in the patient's anatomical model, production method 604 may involve creating a feature vector of the boundary conditions used in the training mode. Production method 604 may then use saved results of the machine learning algorithm to solve for blood flow and/or blood pressure at one or more points of the model or the system represented by the model (e.g., to perform step 308 of method 300 as described in FIG. 3). Finally, production method 604 may include saving the results of the machine learning algorithm, including the solved blood flow and/or blood pressure, to a storage device of server systems 106.

The embodiments of the disclosure include systems and methods of identifying lesions causing weight loss and/or weight gain (e.g., mesenteric ischemia, obstruction in the portal venous system or hepatic artery, etc.), and for treatment planning to stent the appropriate regions of vessel narrowing to restore blood flow.

Figure 7:
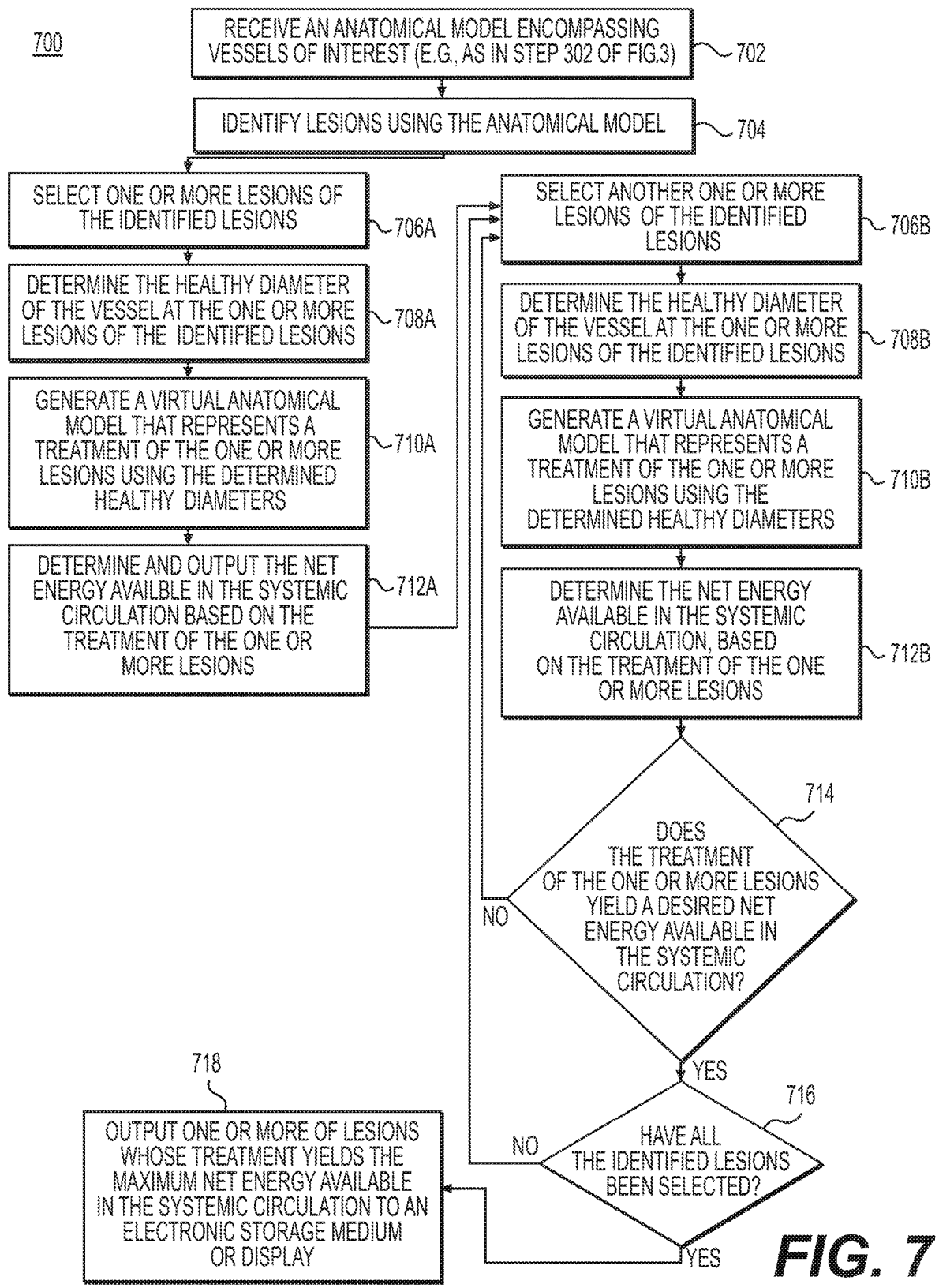
FIG. 7 is a block diagram of an exemplary method of determining lesions that result in weight loss (e.g., via mesenteric, hepatic, and/or portal ischemia), according to an exemplary embodiment of the present disclosure.

FIG. 7 is a block diagram of an exemplary method of determining lesions that result in weight loss (e.g., via mesenteric, hepatic, and/or portal ischemia), according to an exemplary embodiment of the present disclosure.

In one embodiment, step 702 may include receiving an anatomical model encompassing vessels of interest (e.g., as in step 302 of method 300 in FIG. 3). Thus, the anatomical model may be received from or generated from anatomical information and/or images of the vessels of interest. Notably, some of the vessels of interest may include lesions. Subsequent steps of method 700 may aid in the treatment planning of one or more of the lesions via a virtual anatomical model.

Step 704 may include identifying a plurality of lesions to be analyzed, for example, to determine which of the plurality of lesions result in weight loss. The lesions may be identified from the anatomical model or information received in step 702. In some embodiments, step 704 may include identifying all or one or more combinations of lesions using the anatomical information. Step 704 may be performed by a processor of server system 106.

Step 706A may include selecting one or more lesions of (e.g., a subset of) the identified lesions from step 704. Subsequently, step 708A may include determining the healthy diameter for the vessel at the location of one or more selected lesions. The healthy diameter may be determined by evaluating the diameter at proximal and distal vessel locations which are healthy.

Step 710A may include generating a virtual anatomical model that represents a treatment of the selected one or more lesions. The appropriate treatment may be based on the determined healthy diameters from step 708A.

Step 712A may include determining the net energy available in the systemic circulation, based on the treatment of the one or more lesions, and outputting that determination into an electronic storage medium. In some embodiments, step 712A may be performed using the steps 304 through 314 of method 300 as depicted in FIG. 3. For example, the virtual anatomical model generated in step 712A, which represents a treatment of the selected one or more lesions of the identified lesions using the determined healthy diameters, may be truncated at locations to apply appropriate boundary conditions (e.g., as in steps 304 and 306). Then the truncated virtual anatomical model may be used to solve for blood flow and blood pressure through the entire system (e.g., as in step 308), model nutrient transport (e.g., as in step 310), and model blood flow through hepatic vessels and model phasic changes in blood flow in relation to food intake (e.g., as in step 312), in order to determine and output the net energy available in the systemic circulation (e.g., as in step 314), based on the treatment of the selected one or more lesions of the identified lesions. Step 712A may further include storing the determined and output net energy available into an electronic storage medium. In some embodiments, other relevant quantities may also be determined and output into an electronic storage medium. The stored values may be used to compare the net energy available in the systemic circulation, based on the treatment of other selected one or more lesions. Thus, step steps 708A through 712A may be repeated for other selections of one or more lesions of the identified lesions (e.g., as in steps 706B through steps 712B and step 714), and the outputted net energies available in the systemic circulation for each selection may be compared and/or assessed (e.g., as in step 714).

For example, step 706B may include selecting another one or more lesions of the identified lesions from step 704. One or more of the lesions selected in step 706B may be different from the selected one or more lesions of step 706A, for example, to determined the lesion or group of lesions, whose treatment yields the maximum energy available in the systemic circulation. Step 708B may include determining the healthy diameter for the selected one or more lesions in step 706B (e.g., as in step 708A). Step 710B may include generating a virtual anatomical model that represents a treatment of the one or more lesions using the determined healthy diameters (e.g., as in 710A). Likewise, step 712B may include determining the net energy available in the systemic circulation (e.g., as in step 712A), based on the one or more lesions selected in step 706B.

Step 714 may include determining whether the treatment of the selected one or more lesions (e.g., from step 706B) yields a desired and/or maximum net energy available in the systemic circulation. For example, step 714 may include comparing the net energy available in the systemic circulation, as calculated in step 712B for the selected one or more lesions from step 706B, with the net energy available in the systemic circulation, as calculated in step 712A for the selected one or more lesions from step 706A. The values of the net energies, or other relevant quantities of interest to be compared, may be retrieved from an electronic storage medium of server systems 106. In some embodiments, determining the maximum net energy available may involve determining whether among the calculated net energies available, the most recently calculated net energy (e.g., from step 712B) trumps any previously calculated net energy (e.g., from step 712A) that holds as record as the highest or maximum net energy available in the systemic circulation. Thus, in such embodiments, the electronic storage medium may mark or designate a selected group of lesions, whose treatment yields the highest or maximum net energy available in the systemic circulation, and the value of the net energy, as a record. Furthermore, in such embodiments, if the most recently calculated net energy (e.g., from step 712B) trumps any previously held record (e.g., the net energy calculated in 712A), the most recently calculated net energy may replace any previously calculated net energy to hold the record for the highest or maximum net energy available in the systemic circulation. Importantly, in replacing the record, the selected one or more lesions, whose treatment yields the highest or maximum net energy available in the systemic circulation may also be recorded in the electronic storage medium of server systems 106.

If, subsequent to step 714, the treatment of the selected one or more lesions of (e.g., most recently selected in step 706B) does not yield the highest or maximum net energy available in the systemic circulation (e.g., does not beat the currently held record), steps 706B through 712B may be repeated, using another set of one or more lesions of the identified lesions. Subsequently, step 714 may include determining whether the treatment of yet another group one or more lesions yields the highest or maximum net energy available in the systemic circulations.

If, subsequent to step 714, the treatment of a recently selected one or more lesions does yield the maximum energy available in the systemic circulation, step 716 may include determining whether all or a sufficient number of the identified lesions and/or groups of identified lesions have been selected (and/or analyzed using steps 706B through 714). If not, steps 706B through step 714 may be performed for multiple iterations until all or a sufficient number of the identified lesions or groups of lesions have been selected.

If, subsequent to step 716, all or a sufficient number of the identified lesions and/or groups of lesions from step 704 have been selected (and/or analyzed using steps 706B through 714), step 718 may include outputting one or more of the lesions, whose treatment yields the highest or maximum energy available in the systemic circulation to an electronic storage medium or display. In some embodiments, step 718 may involve outputting the currently held record for the maximum net energy available in the systemic circulation and the one or more lesions whose treatment yields that net energy. In some embodiments, step 718 may additionally include determining and outputting the difference between the net energy available in the systemic circulation of an untreated patient and the net energy available in the systemic circulation of the a treated patient (e.g., as determined in step 712A or 712B). Thus, step 718 may include, for example, selecting a combination of one or more lesions, whose difference calculated in step 716 is the largest. In some embodiments, the virtual model of the one or more lesions yielding the highest or maximum net energy available in the blood stream may also be output. In such embodiments, the virtual model may be overlaid with, for example, blood flow characteristics at one or more points of the model.

In other embodiments, method 700 may be adjusted in order to determine one or more lesions, whose treatment yields the highest or maximum value of another relevant quantity of interest (e.g., effective permeability and flowrate, the rate of particle transfer to a blood vessel, the concentration of nutrients along vessels, a blood flow characteristic, etc.).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of modeling nutrient transport within a patient, the method comprising:
    generating a three-dimensional patient-specific anatomical model of at least a portion of a visceral vascular system of the patient based at least on a velocity of blood or a pressure of blood flowing through the visceral vascular system;
    receiving, in an electronic storage medium, patient-specific information related to a patient's food intake;
    determining a boundary condition information of the patient-specific anatomical model of at least a portion of the visceral vascular system;
    generating a patient-specific feature vector using the boundary condition information;
    determining, using a trained machine learning system, the velocity of blood or the pressure of blood flowing through the visceral vascular system using the patient-specific feature vector;
    determining an amount of nutrients in the visceral vascular system using the patient-specific information related to the patient's food intake;
    generating a patient-specific model of blood flow in the patient-specific anatomical model of the portion of the visceral vascular system of the patient using at least (1) the determined velocity of blood or the pressure of blood flowing through the visceral vascular system, and (2) the patient-specific information related to the patient's food intake, wherein the patient-specific model of blood flow includes the amount of nutrients in the visceral vascular system;
    generating a patient-specific model of nutrient transport from at least a part of a gastrointestinal system of the patient to the portion of the visceral vascular system of the patient based on the patient-specific information related to the patient's food intake; and
    determining an indicia of energy available in the patient based on the patient-specific model of nutrient transport and the patient-specific model of blood flow, the indicia of energy indicating a normal or an abnormal function of a liver of the patient.

2. The computer-implemented method of claim 1, further comprising:
simulating blood flow through hepatic and portal blood vessels of the patient based on the patient-specific model of nutrient transport, wherein the blood flow through the hepatic and portal blood vessels transports nutrients.

3. The computer-implemented method of claim 1, further comprising:
truncating the patient-specific anatomical model at one or more locations;
applying boundary conditions at the one or more locations to determine blood flow characteristics in the truncated patient-specific anatomical model; and
generating a patient-specific model of blood flow based on the determined blood flow characteristics in the truncated patient-specific anatomical model.

4. The computer-implemented method of claim 1, wherein the indicia of energy available includes one or more of: a net energy available in systemic circulation or visceral vascular system, a net nutrient available in the systemic circulation or visceral vascular system, a net sugar level in the systemic circulation or visceral vascular system, or a net energy transferred to or from the visceral vascular system.

5. The computer-implemented method of claim 1, wherein the patient-specific information related to the patient's food intake includes one or more of:
a density, an amount, a volume, a mass, a nutritional content, or an acidity of the patient's food intake; and
temporal and/or geographical information of the patient's food intake.

6. The computer-implemented method of claim 1, further comprising:
receiving gastrointestinal health information of the patient;
generating the patient-specific model of nutrient transport from the at least the part of a gastrointestinal system of the patient to the visceral vascular system of the patient based on the patient-specific information related to the patient's food intake and the gastrointestinal health information of the patient; and
determining the indicia of the energy available in systemic circulation of the patient based on the patient-specific model of nutrient transport and the gastrointestinal health information of the patient.

7. The computer-implemented method of claim 6, wherein the gastrointestinal health information includes one or more of:
an indicia of peristaltic function of the gastrointestinal tract of the patient;
an estimated membrane channel permeability of the patient; and
an indicia of mesenteric ischemia of the patient.

8. The computer-implemented method of claim 1, wherein generating the patient-specific model of nutrient transport from at least a part of a gastrointestinal system of the patient to the visceral vascular system of the patient includes one or more of:
modeling a mesenteric flow rate based on one or more of the patient-specific information related to the patient's food intake and gastrointestinal health information of the patient;
modeling a membrane channel permeability of a vessel; or
modeling a concentration gradient of nutrients between the at least the part of the gastrointestinal system of the patient and a visceral vessel based on one or more of the mesenteric flow rate or the membrane channel permeability.

9. The computer-implemented method of claim 1, further comprising:
determining a change in a weight or a mass of the patient based on the determined indicia of energy available in the patient.

10. The computer-implemented method of claim 9, wherein the change in the weight or the mass of the patient is further based on one or more of:
a metabolic rate and/or a metabolic demand of the patient; and
an indicia of insulin resistance of the patient.

11. The computer-implemented method of claim 1, wherein determining, using a trained machine learning system, the velocity of blood or the pressure of blood flowing through the visceral vascular system includes using feature weights obtained during a training of the machine learning system.

12. A system for modeling nutrient transport within a patient, the system comprising:
at least one data storage device storing instructions for modeling nutrient transport within a patient; and
at least one processor configured to execute the instructions to perform a method comprising:
generating a three-dimensional patient-specific anatomical model of at least a portion of a visceral vascular system of the patient based at least on a velocity of blood or a pressure of blood flowing through the visceral vascular system;
receiving, in an electronic storage medium, patient-specific information related to a patient's food intake;
determining a boundary condition information of the patient-specific anatomical model of at least a portion of the visceral vascular system;
determining the velocity of blood or the pressure of blood flowing through the visceral vascular system using the boundary condition information;
generating a patient-specific feature vector using the boundary condition information;
determining, using a trained machine learning system, the velocity of blood or the pressure of blood flowing through the visceral vascular system using the patient-specific feature vector;
determining an amount of nutrients in the visceral vascular system using the patient-specific information related to the patient's food intake;
generating a patient-specific model of blood flow in the patient-specific anatomical model of the portion of the visceral vascular system of the patient using at least (1) the velocity of blood or the pressure of blood flowing through the visceral vascular system, and (2) the patient-specific information related to the patient's food intake, wherein the patient-specific model of blood flow includes the amount of nutrients in the visceral vascular system;
generating a patient-specific model of nutrient transport from at least a part of a gastrointestinal system of the patient to the portion of the visceral vascular system of the patient based on the patient-specific information related to the patient's food intake; and
determining an indicia of energy available in the patient based on the patient-specific model of nutrient transport and the patient-specific model of blood flow, the indicia of energy indicating a normal or an abnormal function of a liver of the patient.

13. The system of claim 12, further comprising:
simulating blood flow through hepatic and portal blood vessels of the patient based on the patient-specific model of nutrient transport, wherein the blood flow through the hepatic and portal blood vessels transports nutrients.

14. The system of claim 12, further comprising:
receiving an indicia of a liver function of the patient, wherein determining the indicia of the energy available in the patient is based on the indicia of the liver function of the patient and the patient-specific model of nutrient transport.

15. The system of claim 12, wherein generating the patient-specific model of nutrient transport from at least a part of a gastrointestinal system of the patient to the visceral vascular system of the patient includes one or more of:
modeling a mesenteric flow rate based on one or more of the patient-specific information related to the patient's food intake and gastrointestinal health information of the patient;
modeling a membrane channel permeability of a vessel; or
modeling a concentration gradient of nutrients between the at least the part of the gastrointestinal system of the patient and a visceral vessel based on one or more of the mesenteric flow rate or the membrane channel permeability.

16. The system of claim 12, further comprising:
determining a change in a weight or mass of the patient based on the determined indicia of the energy available in the patient.

17. A non-transitory computer-readable medium storing instructions that, when executed by a computer, cause the computer to perform a method for modeling nutrient transport within a patient, the method including:
generating a three-dimensional patient-specific anatomical model of at least a portion of a visceral vascular system of the patient based at least on a velocity of blood or a pressure of blood flowing through the visceral vascular system;
receiving, in an electronic storage medium, patient-specific information related to a patient's food intake;
determining a boundary condition information of the patient-specific anatomical model of at least a portion of the visceral vascular system;
determining the velocity of blood or the pressure of blood flowing through the visceral vascular system using the boundary condition information;
generating a patient-specific feature vector using the boundary condition information;
determining, using a trained machine learning system, the velocity of blood or the pressure of blood flowing through the visceral vascular system using the patient-specific feature vector;
determining an amount of nutrients in the visceral vascular system using the patient-specific information related to the patient's food intake;
generating a patient-specific model of blood flow in the patient-specific anatomical model of the portion of the visceral vascular system of the patient using at least (1) the velocity of blood or the pressure of blood flowing through the visceral vascular system, and (2) the patient-specific information related to the patient's food intake, wherein the patient-specific model of blood flow includes the amount of nutrients in the visceral vascular system;
generating a patient-specific model of nutrient transport from at least a part of a gastrointestinal system of the patient to the portion of the visceral vascular system of the patient based on the patient-specific information related to the patient's food intake; and
determining an indicia of energy available in the patient based on the patient-specific model of nutrient transport and the patient-specific model of blood flow, the indicia of energy indicating a normal or an abnormal function of a liver of the patient.

18. The non-transitory computer readable medium of claim 17, further comprising:
simulating blood flow through hepatic and portal blood vessels of the patient based on the patient-specific model of nutrient transport, wherein the blood flow through the hepatic and portal blood vessels transports nutrients.

19. The non-transitory computer readable medium of claim 17, further comprising:
receiving an indicia of a liver function of the patient, wherein determining the indicia of the energy available in the patient is based on the indicia of the liver function of the patient and the patient-specific model of nutrient transport.

20. The non-transitory computer readable medium of claim 17, further comprising:
determining a change in a weight or mass of the patient based on the determined indicia of the energy available in the patient.

* * * * *